United States Patent
Mito et al.

(10) Patent No.: US 12,156,924 B2
(45) Date of Patent: Dec. 3, 2024

(54) INORGANIC POWDER COMPOSITE, METHOD FOR PRODUCING SAME, WATER-IN-OIL EMULSION COMPOSITION, AND SUNSCREEN COSMETIC

(71) Applicant: TAYCA CORPORATION, Osaka (JP)

(72) Inventors: Shunsuke Mito, Osaka (JP); Kenji Kayahara, Osaka (JP); Naoki Kanda, Osaka (JP)

(73) Assignee: TAYCA CORPORATION, Osaka (JP)

( * ) Notice: Subject to any disclaimer, the term of this patent is extended or adjusted under 35 U.S.C. 154(b) by 745 days.

(21) Appl. No.: 17/287,590

(22) PCT Filed: Oct. 18, 2019

(86) PCT No.: PCT/JP2019/041138
§ 371 (c)(1),
(2) Date: Apr. 22, 2021

(87) PCT Pub. No.: WO2020/085241
PCT Pub. Date: Apr. 30, 2020

(65) Prior Publication Data
US 2021/0315781 A1    Oct. 14, 2021

(30) Foreign Application Priority Data

Oct. 24, 2018 (JP) .................. 2018-199682

(51) Int. Cl.
*A61K 8/02* (2006.01)
*A61K 8/06* (2006.01)
*A61K 8/25* (2006.01)
*A61K 8/27* (2006.01)
(Continued)

(52) U.S. Cl.
CPC .............. *A61K 8/022* (2013.01); *A61K 8/064* (2013.01); *A61K 8/25* (2013.01); *A61K 8/27* (2013.01);
(Continued)

(58) Field of Classification Search
CPC .......... A61K 8/022; A61K 8/064; A61K 8/25; A61K 8/27; A61K 8/29; A61K 8/36;
(Continued)

(56) References Cited

U.S. PATENT DOCUMENTS 6,534,044 B1 * 3/2003 Wada ..................... C09C 1/043
424/59
2018/0271757 A1    9/2018 Nagai et al.

FOREIGN PATENT DOCUMENTS

JP    2004210748 A  *  7/2004
JP    2008-94917 A     4/2008
(Continued)

OTHER PUBLICATIONS

Matsumoto Trading, Ultrafine Zinc Oxide for Sunscreens, Apr. 1, 2010. (Year: 2010).*

(Continued)

*Primary Examiner* — Benjamin J Packard
*Assistant Examiner* — Joshua A Atkinson
(74) *Attorney, Agent, or Firm* — Millen White Zelano & Branigan; Csaba Henter

(57) ABSTRACT

Provided is an inorganic powder composite used for a water-in-oil type fine dispersion system which is excellent in emulsification and emulsification stability. The inorganic powder composite includes: an inorganic powder; and a first hydrophobic treatment agent, a second hydrophobic treatment agent, and a hydrophilic treatment agent, which cover at least one part of a surface of the inorganic powder, the first hydrophobic treatment agent is a silicon compound, the second hydrophobic treatment agent is a fatty acid, and the hydrophilic treatment agent is hydrous silica.

22 Claims, 1 Drawing Sheet

(51) Int. Cl.
*A61K 8/29* (2006.01)
*A61K 8/36* (2006.01)
*A61K 8/58* (2006.01)
*A61K 8/891* (2006.01)
*A61Q 17/04* (2006.01)

(52) U.S. Cl.
CPC .................. *A61K 8/29* (2013.01); *A61K 8/36* (2013.01); *A61K 8/585* (2013.01); *A61K 8/891* (2013.01); *A61Q 17/04* (2013.01); *A61K 2800/33* (2013.01); *A61K 2800/413* (2013.01); *A61K 2800/623* (2013.01); *A61K 2800/624* (2013.01); *A61K 2800/805* (2013.01)

(58) Field of Classification Search
CPC .... A61K 8/585; A61K 8/891; A61K 2800/33; A61K 2800/413; A61K 2800/623; A61K 2800/624; A61K 2800/805; A61K 2800/612; A61K 2800/614; A61K 8/0241; A61K 8/361; A61K 8/58; A61Q 17/04; C09C 1/04
See application file for complete search history.

(56) References Cited

FOREIGN PATENT DOCUMENTS

| | | | |
|---|---|---|---|
| JP | 2009161496 A | * | 7/2009 |
| JP | 2012240995 A | * | 12/2012 |
| JP | 2016-141671 A | | 8/2016 |
| JP | 2017-36254 A | | 2/2017 |
| JP | 2017-88421 A | | 5/2017 |
| WO | WO-2016121761 A1 | * | 8/2016 |

OTHER PUBLICATIONS

International Search Report dated Dec. 17, 2019 issued in corresponding PCT/JP2019/041138 application (2 pages).
English Abstract of JP 2008-94917 A published Apr. 24, 2008.
English Abstract of JP 2017-36254 A published Feb. 16, 2017.
English Abstract of JP 2017-88421 A published May 25, 2017.
English Abstract of JP 2016-141671 A published Aug. 8, 2016.

* cited by examiner

INORGANIC POWDER COMPOSITE, METHOD FOR PRODUCING SAME, WATER-IN-OIL EMULSION COMPOSITION, AND SUNSCREEN COSMETIC

TECHNICAL FIELD

The present invention relates generally to inorganic powder composites and, in particular, to an inorganic powder composite used in a water-in-oil type fine dispersion system.

BACKGROUND ART

In an emulsion type sunscreen cosmetic, traditionally, an ultraviolet ray shielding agent or an ultraviolet ray protective agent such as zinc oxide or titanium oxide, which is subjected to hydrophobic surface treatment is blended in an oil phase. In this case, since the ultraviolet ray shielding agent or the ultraviolet ray protective agent is not present in a water phase, ultraviolet rays pass through the water phase in the cosmetic. Therefore, in order to attain further high ultraviolet ray shielding effects or ultraviolet ray protective effects, it is required to increase an amount of the oil phase by blending a further large amount of the ultraviolet ray shielding agent or the ultraviolet ray protective agent. In addition, it is required to maintain stability of a state in which the water phase and the oil phase are emulsified and to prevent the water phase, which passes the ultraviolet rays therethrough, from separating.

However, an emulsifying agent has stickiness which is peculiar to the emulsifying agent, and there may be a case where the stickiness exerts adverse influence on touch and the like of the cosmetic.

Therefore, conventionally, there have been proposed emulsion compositions, each of which does not contain the emulsifying agent.

For example, described in Japanese Unexamined Patent Application Publication No. 2001-518112 (Patent Literature 1) as a cosmetic or a dermatological preparation, which does not contain the emulsifying agent, is a water-in-oil type fine dispersion system which contains an oil phase, a water phase, and fine inorganic pigment which has both properties of hydrophilia and lipophilicity. In Patent Literature 1, as the fine inorganic pigment, titanium dioxide pigment covered with aluminum stearate and zinc oxide pigment covered with dimethylpolysiloxane are described.

In addition, described in Japanese Patent No. 5910632 (Patent Literature 2) is a composite powder which is obtained by forming, on an inorganic powder, a first covering layer which is constituted of a water-repellent organic compound such as silicone oil and forming, on the first coating layer, a second covering layer which is constituted of an Si compound or an Al compound, which is hydrophilic.

CITATION LIST

Patent Literature

Patent Literature 1: Japanese Unexamined Patent Application Publication (Translation of PCT Application) No. 2001-518112
Patent Literature 2: Japanese Patent No. 5910632

SUMMARY OF THE INVENTION

Technical Problem

However, in the water-in-oil type fine dispersion system described in Patent Literature 1, emulsification is not sufficient and emulsification stability is not sufficient. When the emulsification and the emulsification stability are insufficient, separation of the water phase and the oil phase occurs over time, thereby leading to a problem in that touch upon use is impaired, a problem in that sufficient ultraviolet ray protective effects cannot be exhibited, and other problems.

In addition, it is assumed that the composite powder described in Patent Literature 2 is dispersed in water and it is not assumed that an emulsion composition is prepared by using this composite powder without using any emulsifying agent or emulsification stability of the emulsion composition is enhanced.

Therefore, an object of the present invention is to provide an inorganic powder composite which is excellent in emulsification and emulsification stability and is used in a water-in-oil type fine dispersion system.

Solution to Problem

The present inventors have found that by using an inorganic powder composite which is obtained by subjecting an inorganic powder to surface treatment by a first hydrophobic treatment agent, a second hydrophobic treatment agent, and a hydrophilic treatment agent, more specifically, by a silicon compound, a fatty acid, and hydrous silica, a water-in-oil type (W/O type) emulsion composition can be manufactured even without using an emulsifying agent. In addition, the present inventors, have found that this emulsion composition is favorable also in temporal emulsification stability.

Furthermore, the present inventors, have found unexpected effects in that an inorganic powder composite, which is obtained by using, for example, zinc oxide as the inorganic powder and subjecting the inorganic powder to the surface treatment by the silicon compound, the fatty acid, and the hydrous silica, exhibits higher ultraviolet ray protective effects in a case where the inorganic powder composite is in a form of an emulsion composition than in a case where the inorganic powder composite is dispersed in a dispersion medium formed of oil solely. An inorganic powder composite obtained by using the zinc oxide which is subjected to the conventional hydrophobic surface treatment exhibits higher ultraviolet ray protective effects in the case where the inorganic powder composite is dispersed in the dispersion medium formed of the oil solely than in the case where the inorganic powder composite is in the form of the emulsion composition.

Based on the above-described findings made by the present inventors, an inorganic powder composite of the present invention is constituted as follows.

The inorganic powder composite according to the present invention includes: an inorganic powder; and a first hydrophobic treatment agent, a second hydrophobic treatment agent, and a hydrophilic treatment agent, which cover at least one part of a surface of the inorganic powder, the first hydrophobic treatment agent is a silicon compound, the second hydrophobic treatment agent is a fatty acid, and the hydrophilic treatment agent is hydrous silica.

Advantageous Effects of the Invention

According to the present invention, an inorganic powder composite which is excellent in emulsification and emulsification stability and is used in a water-in-oil type fine dispersion system can be provided.

DESCRIPTION OF EMBODIMENT

Figure 1:
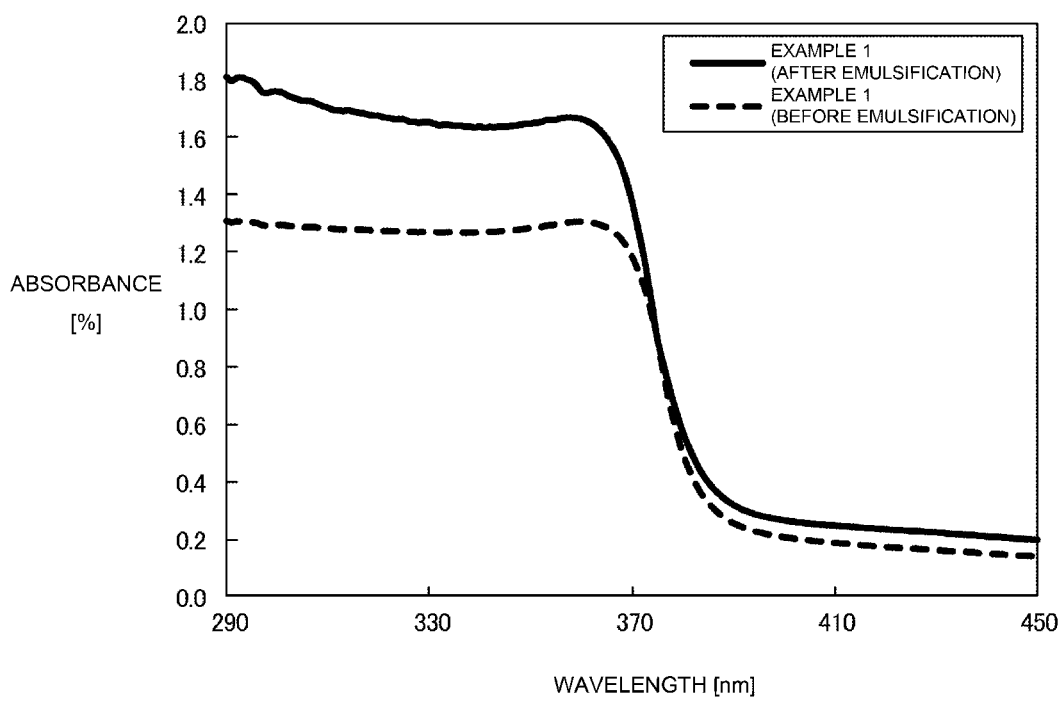
FIG. 1 is a graph showing absorbance of an oil phase at 290 nm to 450 nm before emulsification and absorbance of the oil phase at 290 nm to 450 nm after the emulsification in Example 1.

Hereinafter, an embodiment of the present invention will be described. Note that the present invention is not limited to the below-described embodiment and a variety of modifications can be made without departing from the scope of the technical idea of the present invention.

An inorganic powder composite according to the present invention includes: an inorganic powder; and a first hydrophobic treatment agent, a second hydrophobic treatment agent, and a hydrophilic treatment agent which cover at least one part of a surface of the inorganic powder. The first hydrophobic treatment agent is a silicon compound, the second hydrophobic treatment agent is a fatty acid, and the hydrophilic treatment agent is hydrous silica.

It is preferable that the inorganic powder has ultraviolet ray shielding effects. As the inorganic powder having the ultraviolet ray shielding effects, for example, zinc oxide or titanium oxide can be used.

It is preferable that an average primary particle size of the inorganic powder is less than 80 nm. Note that the average primary particle size in the present invention is obtained by photographing the inorganic powder by means of a transmission-type electron microscope (the number of photographed particles is 1,000 or more), obtaining an equivalent circle diameter by subjecting the photographed individual particles to image processing by means of an image analysis type particle size distribution measuring apparatus, and calculating the average primary particle size from the obtained equivalent circle diameter.

As the first hydrophobic treatment agent (silicon compound), silicone oil such as hydrogen dimethicone, dimethicone, and methylphenyl polysiloxane and a silane compound such as alkylsilane and a silane coupling agent are cited, and it is preferable that the first hydrophobic treatment agent is the hydrogen dimethicone among these or triethoxycaprylylsilane.

It is preferable that an amount of the first hydrophobic treatment agent is 0.5% to 5.0% by weight with respect to the inorganic powder and it is more preferable that the amount of the first hydrophobic treatment agent is 1.0% to 4.0% by weight with respect thereto.

As the second hydrophobic treatment agent (fatty acid), isostearic acid, stearic acid, lauric acid, myristic acid, palmitic acid, and the like are cited, and it is preferable that the second hydrophobic treatment agent is the isostearic acid.

It is preferable that an amount of the second hydrophobic treatment agent is 0.5% to 5.0% by weight with respect to the inorganic powder and it is more preferable that the amount of the second hydrophobic treatment agent is 1.0% to 4.0% by weight with respect thereto.

As a combination of the first hydrophobic treatment agent and the second hydrophobic treatment agent, it is preferable that the first hydrophobic treatment agent is the hydrogen dimethicone or the triethoxycaprylylsilane and the second hydrophobic treatment agent is the isostearic acid.

By using the silicon compound as the first hydrophobic treatment agent, affinity with a silicon-based material such as the silicone oil among oil phase materials is enhanced in particular. On the other hand, by using the fatty acid as the second hydrophobic treatment agent, affinity with a non-silicon-based material such as hydrocarbon oil and ester oil among the oil phase materials is enhanced in particular. By using the first hydrophobic treatment agent and the second hydrophobic treatment agent in combination, easy blending with various and diverse oil phase materials is enabled, thereby allowing sufficient emulsification effects with a wide variety of pharmaceuticals to be exhibited upon preparing the later-described water-in-oil type emulsion composition without being limited to a specific oil phase material.

As a raw material of the hydrophilic treatment agent (hydrous silica), as materials which can form the hydrous silica on the inorganic powder after surface treatment, for example, tetraethyl orthosilicate, methyl silicate oligomer, sodium silicate, and the like are cited, and it is preferable that the raw material of the hydrophilic treatment agent is the tetraethyl orthosilicate or the methyl silicate oligomer.

It is preferable that an amount of the hydrophilic treatment agent is 0.5% to 6.0% by weight with respect to the inorganic powder in terms of $SiO_2$ and it is more preferable that the amount of the hydrophilic treatment agent is 1.0% to 4.0% by weight with respect thereto in terms thereof.

As to a ratio of treatment amounts of the treatment agents, it is preferable that a ratio by weight of the hydrophobic treatment agent (a total of the first hydrophobic treatment agent and the second hydrophobic treatment agent) and the hydrophilic treatment agent, that is, a value of (a total weight of the first hydrophobic treatment agent and the second hydrophobic treatment agent)/(a weight of the hydrophilic treatment agent) is 0.2 to 6.0 and it is more preferable that the above-mentioned value is 0.8 to 2.5.

By making the preparation as described above, the inorganic powder composite used in the water-in-oil type fine dispersion system which is excellent in the emulsification and the emulsification stability can be provided.

Next, a method for manufacturing the inorganic powder composite according to the present invention will be described.

The method for manufacturing the inorganic powder composite includes a step of subjecting the inorganic powder to surface treatment by the first hydrophobic treatment agent, the second hydrophobic treatment agent, and the hydrophilic treatment agent.

As the step of subjecting the inorganic powder to the surface treatment, specifically, a step of performing the surface treatment by simultaneously blending raw materials of the inorganic powder, the first hydrophobic treatment agent, the second hydrophobic treatment agent, and the hydrophilic treatment agent and a step of performing the surface treatment by blending the inorganic powder and the treatment agents in any order are cited. Upon conducting the step of subjecting the inorganic powder to the surface treatment, the surface treatment may be conducted by a dry process without using a dispersion medium, or the surface treatment may be conducted by a wet process by using the dispersion medium. When the dispersion medium is used, although a kind of the dispersion medium is not particularly limited, from a viewpoint of affinity between the inorganic powder and the treatment agents, it is preferable that alcohol such as isopropyl alcohol is used.

After conducting the surface treatment as described above, a drying step and a pulverizing step are optionally conducted, thereby allowing the inorganic powder composite of the present invention to be obtained.

Next, the water-in-oil type emulsion composition using the inorganic powder composite of the present invention will be described.

The water-in-oil type emulsion composition according to the present invention includes the inorganic powder composite of the present invention and preferably, contains no surfactant (emulsifying agent).

It is preferable that the water-in-oil type emulsion composition includes at least one of surface-treated titanium oxide, surface-treated zinc oxide, and an ultraviolet ray absorbing agent.

In the water-in-oil type emulsion composition, it is preferable that a surface treatment agent of the surface-treated titanium oxide or the surface-treated zinc oxide is at least one of hydrous silica, aluminum hydroxide, alginic acid, a fatty acid (more preferably, at least one of lauric acid, myristic acid, palmitic acid, isostearic acid, and stearic acid), silicone oil (more preferably, at least one of methicone, dimethicone, and hydrogen dimethicone), and a silane coupling agent (more preferably, triethoxycaprylylsilane).

In the water-in-oil type emulsion composition, it is preferable that the ultraviolet ray absorbing agent is at least one of a triazine system, a benzotriazole system, a benzophenone system, a merocyanine system, a cyanine system, a dibenzoyl-methane system, a cinnamic acid system, a cyanoacrylate system, and a benzoic acid ester system.

It is preferable that the water-in-oil type emulsion composition according to the present invention is used as, for example, a cosmetic. Thus, it is not required to use the emulsifying agent in the cosmetic, and cosmetics having favorable temporal emulsification stability can be obtained.

In particular, when the zinc oxide is used as the inorganic powder, it is preferable that the water-in-oil type emulsion composition of the present invention is used as a sunscreen cosmetic. Even when an applied part gets wet with water, the sunscreen cosmetic using the water-in-oil type emulsion composition of the present invention can maintain high ultraviolet ray protective effects.

Furthermore, the inorganic powder composite is manufactured by using the zinc oxide as the inorganic powder and the water-in-oil type emulsion composition is manufactured by concurrently using the above-described surface-treated titanium oxide, thereby more enhancing the ultraviolet ray protective effects than the conventional water-in-oil type emulsion composition manufactured by using zinc oxide and titanium oxide in combination. By using this water-in-oil type emulsion composition, a sunscreen cosmetic which exhibits further high ultraviolet ray protective effects can be provided. In other words, a sunscreen cosmetic, even in a small amount, which allows ultraviolet ray protective effects whose degree is the same as the conventional degree or more to be obtained can be provided.

The present invention is summarized as follows.

(1) The inorganic powder composite according to the present invention includes: the inorganic powder; and the first hydrophobic treatment agent, the second hydrophobic treatment agent, and the hydrophilic treatment agent which cover at least one part of the surface of the inorganic powder, the first hydrophobic treatment agent is the silicon compound, the second hydrophobic treatment agent is the fatty acid, and the hydrophilic treatment agent is the hydrous silica.

(2) In the inorganic powder composite according to the present invention, it is preferable that the inorganic powder has the ultraviolet ray shielding effects.

(3) In the inorganic powder composite according to the present invention, it is preferable that the inorganic powder is the zinc oxide.

(4) In the inorganic powder composite according to the present invention, it is preferable that the first hydrophobic treatment agent is the hydrogen dimethicone or the triethoxycaprylylsilane.

(5) In the inorganic powder composite according to the present invention, it is preferable that the second hydrophobic treatment agent is the isostearic acid.

(6) In the inorganic powder composite according to the present invention, it is preferable that the first hydrophobic treatment agent is the hydrogen dimethicone or the triethoxycaprylylsilane and the second hydrophobic treatment agent is the isostearic acid.

(7) In the inorganic powder composite according to the present invention, it is preferable that the average primary particle size of the inorganic powder is less than 80 nm.

(8) It is preferable that the inorganic powder composite according to the present invention includes 90% to 98% by weight of the inorganic powder, 0.5% to 5.0% by weight of the first hydrophobic treatment agent, 0.5% to 5.0% by weight of the second hydrophobic treatment agent, and 0.5% to 6.0% by weight of the hydrophilic treatment agent in terms of $SiO_2$.

(9) It is preferable that when an emulsion is obtained by adding 25 g of the inorganic powder composite to 50 g of the decamethylcyclopentasiloxane, dispersing the resultant for three minutes at 3000 rpm by means of a disperser to thereby obtain an oil phase dispersion, adding 25 g of water to the oil phase dispersion, and emulsifying the resultant for two minutes at 3000 rpm by means of the disperser, the emulsion of the inorganic powder composite according to the present invention maintains an emulsified state after the emulsion has been stored at 50° C. for one week.

(10) It is preferable that an SPF of the emulsion of the inorganic powder composite according to the present invention is 1.5 times or more as large as an SPF of an oil phase dispersion obtained by adding 25 g of the inorganic powder composite to 75 g of the decamethylcyclopentasiloxane and dispersing the resultant for three minutes at 3000 rpm by means of the disperser.

(11) The water-in-oil type emulsion composition according to one aspect of the present invention includes any of the above-mentioned inorganic powder composites.

(12) The water-in-oil type emulsion composition according to another aspect of the present invention includes any of the above-mentioned inorganic powder composites and contains no surfactant.

(13) It is preferable that the water-in-oil type emulsion composition according to the present invention further includes at least one of the surface-treated titanium oxide, the surface-treated zinc oxide, and the ultraviolet ray absorbing agent.

(14) In the water-in-oil type emulsion composition according to the present invention, it is preferable that the surface treatment agent of the surface-treated titanium oxide or the surface-treated zinc oxide is at least one of the hydrous silica, the aluminum hydroxide, the alginic acid, the fatty acid, the silicone oil, and the silane coupling agent.

(15) In the water-in-oil type emulsion composition according to the present invention, it is preferable that the fatty acid is at least one of the lauric acid, the myristic acid, the palmitic acid, the isostearic acid, and the stearic acid.

(16) In the water-in-oil type emulsion composition according to the present invention, it is preferable that the silicone oil is at least one of the methicone, the dimethicone, and the hydrogen dimethicone.

(17) In the water-in-oil type emulsion composition according to the present invention, it is preferable that the silane coupling agent is the triethoxycaprylylsilane.

(18) In the water-in-oil type emulsion composition according to the present invention, it is preferable that the ultraviolet ray absorbing agent is at least one of the triazine system, the benzotriazole system, the benzophenone system, the merocyanine system, the cyanine system, the dibenzoyl-methane system the cinnamic acid system, the cyanoacrylate system, and the benzoic acid ester system.

(19) It is preferable that the water-in-oil type emulsion composition according to the present invention is the sunscreen cosmetic.

(20) The method for manufacturing an inorganic powder composite according to the present invention includes a step of subjecting the inorganic powder to the surface treatment by the first hydrophobic treatment agent, the second hydrophobic treatment agent, and the hydrophilic treatment agent, and the first hydrophobic treatment agent is the silicon compound, the second hydrophobic treatment agent is the fatty acid, and the hydrophilic treatment agent is the hydrous silica.

(21) In the method for manufacturing the inorganic powder composite according to the present invention, it is preferable that the first hydrophobic treatment agent is the hydrogen dimethicone or the triethoxycaprylylsilane and the second hydrophobic treatment agent is the isostearic acid.

EXAMPLES

Example 1

One hundred g of a zinc oxide base material (manufactured by TAYCA CORPORATION: MZ-500) having an average primary particle size of 25 nm as an inorganic powder; 2.6 g of hydrogen dimethicone (manufactured by Shin-Etsu Chemical Co., Ltd.: KF-9901) as a first hydrophobic treatment agent; 1.4 g of isostearic acid (manufactured by KOKYU ALCOHOL KOGYO CO., LTD.: ISOSTEARIC ACID EX) as a second hydrophobic treatment agent; and 10.4 g of tetraethyl orthosilicate (manufactured by Shin-Etsu Chemical Co., Ltd.: KBE-04) as a hydrophilic treatment agent were blended and were agitated for 20 minutes by a desktop blender, and a step of surface treatment was conducted. After the surface treatment, the obtained powder was inputted into a drying machine and was dried for two hours at 105° C. and was pulverized by a jet mill, thereby obtaining an inorganic powder composite in Example 1. Note that the average primary particle size of the inorganic powder was measured by photographing individual particles by means of a transmission-type electron microscope (manufactured by JEOL Ltd.) and conducting image processing by image analysis type particle size distribution software Mac-VIEW (manufactured by Mountech Co., Ltd.).

Example 2

One hundred g of a zinc oxide base material (manufactured by TAYCA CORPORATION: MZ-500) having an average primary particle size of 25 nm as an inorganic powder; 2.6 g of hydrogen dimethicone (manufactured by Shin-Etsu Chemical Co., Ltd.: KF-9901) as a first hydrophobic treatment agent; 1.4 g of isostearic acid (manufactured by KOKYU ALCOHOL KOGYO CO., LTD.: ISOSTEARIC ACID EX) as a second hydrophobic treatment agent; 10.4 g of tetraethyl orthosilicate (manufactured by Shin-Etsu Chemical Co., Ltd.: KBE-04) as a hydrophilic treatment agent; and 300 g of isopropyl alcohol were blended, crushing processing was conducted by means of a sand grinder mill, and thereafter, reduced-pressure distillation was conducted, thereby distilling away the isopropyl alcohol. The obtained treated product was inputted into a drying machine, was dried for two hours at 105° C., and was pulverized by means of a jet mill, thereby obtaining an inorganic powder composite in Example 2.

Examples 3 to 5

Inorganic powder composites in Examples 3 to 5 were obtained by employing a method similar to the method employed in Example 1 except that zinc oxide base materials (any of which was manufactured by TAYCA CORPORATION) and treatment agents show in Table 1 were used.

Example 6

An inorganic powder composite in Example 6 was obtained by using a zinc oxide base material and treatment agents shown in Table 1 and by employing a method similar to the method employed in Example 1 except that as a hydrophilic treatment agent in particular, 5.8 g of methyl silicate oligomer (manufactured by Mitsubishi Chemical Corporation: MS-51), changed from the tetraethyl orthosilicate, was used.

Example 7

An inorganic powder composite in Example 7 was obtained by using a zinc oxide base material and treatment agents shown in Table 1 and by employing a method similar to the method employed in Example 1 except that as the zinc oxide base material in particular, a zinc oxide base material having an average primary particle size of 80 nm was used.

Comparative Examples 1 to 3

Inorganic powder composites in Comparative Examples 1 to 3 were obtained by employing a method similar to the method employed in Example 1 except that zinc oxide base materials (any of which was manufactured by TAYCA CORPORATION) and treatment agents shown in Table 1 were used.

Comparative Example 4

As an inorganic powder, 100 g of a zinc oxide powder (manufactured by TAYCA CORPORATION: MZ-500) having an average primary particle size of 25 nm and as a hydrophilic treatment agent, 48 g of methyl silicate oligomer (manufactured by Mitsubishi Chemical Corporation: MS-51), and 310 g of isopropyl alcohol were blended and reduced-pressure distillation was conducted, thereby distilling away the isopropyl alcohol. The obtained treated product was inputted into a drying machine, was dried for two hours at 130° C., was pulverized by means of a jet mill, thereby obtaining an inorganic powder composite in Comparative Example 4.

Comparative Example 5

In accordance with Example 1 in Japanese Patent No. 5910632, an inorganic powder composite in Comparative Example 5 was obtained. However, instead of zinc oxide (Sakai Chemical Industry Co., Ltd.: FINEX-50S-LP2) treated with 4%-hydrogen dimethicone, a zinc oxide base material (manufactured by TAYCA CORPORATION: MZ-500) treated with 4%-hydrogen dimethicone was used.

TABLE 1

| | | | | | First Hydrophobic Treatment Agent | | Second Hydrophobic Treatment Agent | |
|---|---|---|---|---|---|---|---|---|
| | | Inorganic Powder | | | | | | |
| | Kind | (Product Name) | Average Primary Particle Size (nm) | Used Amount (g) | Kind | Used Amount (g) | Kind | Used Amount (g) |
| Example 1 | zinc oxide | MZ-500 | 25 | 100.0 | hydrogen dimethicone | 2.6 | isostearic acid | 1.4 |
| Example 2 | zinc oxide | MZ-500 | 25 | 100.0 | hydrogen dimethicone | 2.6 | isostearic acid | 1.4 |
| Example 3 | zinc oxide | MZ-300 | 35 | 100.0 | hydrogen dimethicone | 1.3 | isostearic acid | 0.7 |
| Example 4 | zinc oxide | MZ-700 | 50 | 100.0 | hydrogen dimethicone | 0.9 | isostearic acid | 0.5 |
| Example 5 | zinc oxide | MZ-200 | 15 | 100.0 | hydrogen dimethicone | 2.9 | isostearic acid | 1.6 |
| Example 6 | zinc oxide | MZ-500 | 25 | 100.0 | hydrogen dimethicone | 2.6 | isostearic acid | 1.4 |
| Example 7 | zinc oxide | MZ-150 | 80 | 100.0 | hydrogen dimethicone | 0.6 | isostearic acid | 0.3 |
| Comparative Example 1 | zinc oxide | MZ-500 | 25 | 100.0 | hydrogen dimethicone | 5.3 | — | — |
| Comparative Example 2 | zinc oxide | MZ-300 | 35 | 100.0 | hydrogen dimethicone | 3.0 | — | — |
| Comparative Example 3 | zinc oxide | MZ-500 | 25 | 100.0 | — | — | isostearic acid | 5.3 |
| Comparative Example 4 | zinc oxide | MZ-500 | 25 | 100.0 | — | — | — | — |
| Comparative Example 5 | zinc oxide | MZ-500 | 25 | 100.0 | hydrogen dimethicone | 4.0 | — | — |

| | Composition of Inorganic Powder Composite Hydrophilic Treatment Agent | | | Balance of Hydrophobicity/ Hydrophilicity | Treatment Method | Physical Properties (Water-Repellency) of Inorganic Powder Composite |
|---|---|---|---|---|---|---|
| | Kind | Used Amount (g) | $SiO_2$ (g) | | | |
| Example 1 | tetraethyl orthosilicate | 10.4 | 3.0 | 1.3 | dry process | ○ |
| Example 2 | tetraethyl orthosilicate | 10.4 | 3.0 | 1.3 | wet process | ○ |
| Example 3 | tetraethyl orthosilicate | 5.5 | 1.6 | 1.3 | dry process | ○ |
| Example 4 | tetraethyl orthosilicate | 3.5 | 1.0 | 1.4 | dry process | ○ |
| Example 5 | tetraethyl orthosilicate | 11.4 | 3.3 | 1.4 | dry process | ○ |
| Example 6 | methyl silicate oligomer | 5.8 | 3.0 | 1.3 | dry process | ○ |
| Example 7 | tetraethyl orthosilicate | 2.4 | 0.7 | 1.3 | dry process | ○ |
| Comparative Example 1 | — | — | — | only hydrophobicity | dry process | ○ |
| Comparative Example 2 | — | — | — | only hydrophobicity | dry process | ○ |
| Comparative Example 3 | — | — | — | only hydrophobicity | dry process | ○ |
| Comparative Example 4 | methyl silicate oligomer | 48.0 | 25.0 | only hydrophilicity | wet process | x |
| Comparative Example 5 | sodium silicate | 15.4 | 11.6 | 0.3 | wet process | x |

As to physical properties (water-repellency) of the inorganic powder composite, 0.2 g of the powder was added to 20 g of water and the resultant was shaken at 10 times, and thereafter, a state thereof was observed. When the whole amount of the powder floated on the water, a mark "○" was entered in Tables, and when the powder suspended in the water, a mark "x" was entered therein.

In addition, as shown in Table 2, inorganic powder composites in Examples 8 to 10 were obtained in a manner similar to the manner in Example 1 except that kinds and/or amounts of each of the first hydrophobic treatment agent and the second hydrophobic treatment agent were changed.

TABLE 2

| | Composition of Inorganic Powder Composite | | | | | | | |
|---|---|---|---|---|---|---|---|---|
| | Inorganic Powder | | | | First Hydrophobic Treatment Agent | | Second Hydrophobic Treatment Agent | |
| | Kind | (Product Name) | Average Primary Particle Size (nm) | Used Amount (g) | Kind | Used Amount (g) | Kind | Used Amount (g) |
| Example 8 | zinc oxide | MZ-500 | 25 | 100.0 | triethoxy-caprylylsilane | 2.6 | isostearic acid | 1.4 |
| Example 9 | zinc oxide | MZ-500 | 25 | 100.0 | hydrogen dimethicone | 2.0 | isostearic acid | 2.0 |
| Example 10 | zinc oxide | MZ-500 | 25 | 100.0 | hydrogen dimethicone | 1.4 | isostearic acid | 2.6 |

| | Composition of Inorganic Powder Composite Hydrophilic Treatment Agent | | | Balance of Hydrophobicity/ Hydrophilicity | Treatment Method | Physical Properties (Water-Repellency) of Inorganic Powder Composite |
|---|---|---|---|---|---|---|
| | Kind | Used Amount (g) | $SiO_2$ (g) | | | |
| Example 8 | tetraethyl orthosilicate | 10.4 | 3.0 | 1.3 | dry process | ○ |
| Example 9 | tetraethyl orthosilicate | 10.4 | 3.0 | 1.3 | dry process | ○ |
| Example 10 | tetraethyl orthosilicate | 10.4 | 3.0 | 1.3 | dry process | ○ |

In addition, as shown in Table 3, inorganic powder composites in Examples 11 to 15 and Comparative Examples 6 and 7 were obtained in a manner similar to the manner in Example 1 except that amounts of each of the hydrophilic treatment agent and the hydrophobic treatment agent were changed.

TABLE 3

| | Composition of Inorganic Powder Composite | | | | | | | |
|---|---|---|---|---|---|---|---|---|
| | Inorganic Powder | | | | First Hydrophobic Treatment Agent | | Second Hydrophobic Treatment Agent | |
| | Kind | (Product Name) | Average Primary Particle Size (nm) | Used Amount (g) | Kind | Used Amount (g) | Kind | Used Amount (g) |
| Comparative Example 6 | zinc oxide | MZ-500 | 25 | 100.0 | hydrogen dimethicone | 4.6 | isostearic acid | 2.4 |
| Example 11 | zinc oxide | MZ-500 | 25 | 100.0 | hydrogen dimethicone | 3.8 | isostearic acid | 2.2 |
| Example 12 | zinc oxide | MZ-500 | 25 | 100.0 | hydrogen dimethicone | 3.2 | isostearic acid | 1.8 |
| Example 13 | zinc oxide | MZ-500 | 25 | 100.0 | hydrogen dimethicone | 2.0 | isostearic acid | 1.0 |
| Example 14 | zinc oxide | MZ-500 | 25 | 100.0 | hydrogen dimethicone | 1.4 | isostearic acid | 0.6 |
| Example 15 | zinc oxide | MZ-500 | 25 | 100.0 | hydrogen dimethicone | 0.8 | isostearic acid | 0.2 |

TABLE 3-continued

| | Kind | (Product Name) | Average Primary Particle Size (nm) | Used Amount (g) | | | | |
|---|---|---|---|---|---|---|---|---|
| Comparative Example 7 | zinc oxide | MZ-500 | 25 | 100.0 | — | — | — | — |

| | | Composition of Inorganic Powder Composite Hydrophilic Treatment Agent | | | Balance of Hydrophobicity/ Hydrophilicity | Treatment Method | Physical Properties (Water-Repellency) of Inorganic Powder Composite |
|---|---|---|---|---|---|---|---|
| | | Kind | Used Amount (g) | SiO₂ (g) | | | |
| | Comparative Example 6 | □ | □ | — | only hydrophobicity | dry process | ○ |
| | Example 11 | tetraethyl orthosilicate | 3.5 | 1.0 | 6.0 | dry process | ○ |
| | Example 12 | tetraethyl orthosilicate | 6.9 | 2.0 | 2.5 | dry process | ○ |
| | Example 13 | tetraethyl orthosilicate | 13.9 | 4.0 | 0.8 | dry process | ○ |
| | Example 14 | tetraethyl orthosilicate | 17.3 | 5.0 | 0.4 | dry process | ○ |
| | Example 15 | tetraethyl orthosilicate | 20.8 | 6.0 | 0.2 | dry process | ○ |
| | Comparative Example 7 | tetraethyl orthosilicate | 24.3 | 7.0 | only hydrophilicity | dry process | ○ |

In addition, as shown in Table 4, inorganic powder composites in Examples 16 to 20 were obtained in a manner similar to the manner in Example 1 except that kinds and/or amounts were changed.

TABLE 4

Composition of Inorganic Powder Composite

| | Inorganic Powder | | | | First Hydrophobic Treatment Agent | | Second Hydrophobic Treatment Agent | |
|---|---|---|---|---|---|---|---|---|
| | Kind | (Product Name) | Average Primary Particle Size (nm) | Used Amount (g) | Kind | Used Amount (g) | Kind | Used Amount (g) |
| Example 16 | zinc oxide | MZ-500 | 25 | 100.0 | dimethicone | 2.6 | isostearic acid | 1.4 |
| Example 17 | zinc oxide | MZ-500 | 25 | 100.0 | hydrogen dimethicone | 2.6 | lauric acid | 1.4 |
| Example 18 | zinc oxide | MZ-500 | 25 | 100.0 | hydrogen dimethicone | 2.6 | myristic acid | 1.4 |
| Example 19 | zinc oxide | MZ-500 | 25 | 100.0 | hydrogen dimethicone | 2.6 | palmitic acid | 1.4 |
| Example 20 | zinc oxide | MZ-500 | 25 | 100.0 | hydrogen dimethicone | 2.6 | stearic acid | 1.4 |

| | Composition of Inorganic Powder Composite Hydrophilic Treatment Agent | | | Balance of Hydrophobicity/ Hydrophilicity | Treatment Method | Physical Properties (Water-Repellency) of Inorganic Powder Composite |
|---|---|---|---|---|---|---|
| | Kind | Used Amount (g) | SiO₂ (g) | | | |
| Example 16 | tetraethyl orthosilicate | 10.4 | 3.0 | 1.3 | dry process | ○ |
| Example 17 | tetraethyl orthosilicate | 10.4 | 3.0 | 1.3 | dry process | ○ |
| Example 18 | tetraethyl orthosilicate | 10.4 | 3.0 | 1.3 | dry process | ○ |

TABLE 4-continued

| | | | | | | |
|---|---|---|---|---|---|---|
| Example 19 | tetraethyl orthosilicate | 10.4 | 3.0 | 1.3 | dry process | ○ |
| Example 20 | tetraethyl orthosilicate | 10.4 | 3.0 | 1.3 | dry process | ○ |

(Emulsification Stability Test)

Emulsification stability of each of the obtained inorganic powder composites in Examples and Comparative Examples was checked as follows. Results are shown in Tables 5 to 8. First, 25 g of each of the powders in Examples and Comparative Examples was added to 50 g of D5 oil (decamethylcyclopentasiloxane) and the resultant was dispersed for three minutes at 3000 rpm by means of DISPER. Next, 25 g of water was added to the resultant, and the resultant was emulsified for two minutes at 3000 rpm by means of DISPER. Note that each of inorganic power composites in Comparative Example 1A and Comparative Example 2A shown in Table 5 were obtained by adding an emulsifying agent (manufactured by Silicone Division, Shin-Etsu Chemical Co., Ltd.: KF-6028P) to each of the inorganic power composites in Comparative Examples 1 and 2 since the inorganic power composites in Comparative Examples 1 and 2 were not emulsified.

Each of the obtained emulsion compositions was transferred to a test tube and it was checked visually from an immediate lateral direction whether the water was separated. In addition, each of the emulsion compositions was stored at 50° C. and it was checked visually from an immediate lateral direction whether the water was separated. When the water was not separated, a mark "○" was entered in Tables 5 to 8, and when the water was separated, a mark "x" was entered therein.

TABLE 5

| | Emulsion Composition | | | | | | |
|---|---|---|---|---|---|---|---|
| | Oil Phase | | | | Water phase | Oil Phase Dispersoid Evaluation | |
| | Inorganic Powder Composite | | Oil | Emulsifying Agent | | Ultraviolet Ray Shielding | |
| Kind | Average Primary Particle Size (nm) | (g) | D5 oil (g) | KF-6028P (g) | Water (g) | SPF | UVAPF |
| Example 1 | 25 | 25 | 50 | — | 25 | 22 | 12 |
| Example 2 | 25 | 25 | 50 | — | 25 | 21 | 13 |
| Example 3 | 35 | 25 | 50 | — | 25 | 23 | 15 |
| Example 4 | 50 | 25 | 50 | — | 25 | 20 | 16 |
| Example 5 | 15 | 25 | 50 | — | 25 | 21 | 10 |
| Example 6 | 25 | 25 | 50 | — | 25 | 21 | 11 |
| Example 7 | 80 | 25 | 50 | — | 25 | 17 | 15 |
| Comparative Example 1 | 35 | 25 | 50 | — | 25 | 22 | 11 |
| Comparative Example 1A | 35 | 25 | 49.5 | 0.5 | 25 | — | — |
| Comparative Example 2 | 25 | 25 | 50 | — | 25 | 24 | 14 |
| Comparative Example 2A | 25 | 25 | 49.5 | 0.5 | 25 | — | — |
| Comparative Example 3 | 35 | 25 | 50 | — | 25 | 22 | 12 |
| Comparative Example 4 | 35 | 25 | 50 | — | 25 | Unmeasurable since no dispersion was made. | Unmeasurable since no dispersion was made. |
| Comparative Example 5 | 25 | 25 | 50 | — | 25 | Unmeasurable since no dispersion was made. | Unmeasurable since no dispersion was made. |

| | W/O Emulsion Evaluation | | | | | |
|---|---|---|---|---|---|---|
| | Emulsification Stability | | Water Resistance | | | |
| | Immediately After | One Week | Before Water Resistance Test | | After Water Resistance Test | |
| Kind | Emulsification | Later | SPF | UVAPF | SPF | UVAPF |
| Example 1 | ○ | ○ | 41 | 14 | 34 | 13 |
| Example 2 | ○ | ○ | 39 | 14 | 33 | 13 |
| Example 3 | ○ | ○ | 45 | 19 | 40 | 16 |
| Example 4 | ○ | ○ | 40 | 24 | 34 | 20 |
| Example 5 | ○ | ○ | 39 | 13 | 35 | 11 |

TABLE 5-continued

|  |  |  |  |  |  |  |
|---|---|---|---|---|---|---|
| Example 6 | ○ | ○ | 39 | 12 | 31 | 12 |
| Example 7 | ○ | ○ | 22 | 10 | 19 | 8 |
| Comparative Example 1 | x | x | Unmeasurable since no emulsification was made. | Unmeasurable since no emulsification was made. | Unmeasurable since no emulsification was made. | Unmeasurable since no emulsification was made. |
| Comparative Example 1A | ○ | ○ | 20 | 10 | 19 | 11 |
| Comparative Example 2 | x | x | Unmeasurable since no emulsification was made. | Unmeasurable since no emulsification was made. | Unmeasurable since no emulsification was made. | Unmeasurable since no emulsification was made. |
| Comparative Example 2A | ○ | ○ | 21 | 13 | 20 | 11 |
| Comparative Example 3 | x | x | Unmeasurable since no emulsification was made, | Unmeasurable since no emulsification was made. | Unmeasurable since no emulsification was made. | Unmeasurable since no emulsification was made. |
| Comparative Example 4 | x | x | Unmeasurable since no emulsification was made. | Unmeasurable since no emulsification was made. | Unmeasurable since no emulsification was made. | Unmeasurable since no emulsification was made. |
| Comparative Example 5 | x | x | Unmeasurable since no emulsification was made. | Unmeasurable since no emulsification was made. | Unmeasurable since no emulsification was made. | Unmeasurable since no emulsification was made. |

TABLE 6

| Emulsion Composition | | | | | | | | | | | |
|---|---|---|---|---|---|---|---|---|---|---|---|
| Oil Phase | | | | | Oil Phase Dispersoid Evaluation | | W/O Emulsion Evaluation | | | | |
| Inorganic Powder Composite | | | | | | | Emulsification Stability | | Water Resistance | | |
| | Average Primary Particle Size | Oil D5 oil | Emulsifying Agent KF-6028P | Water Phase Water | Ultraviolet Ray Shielding | | Immediately After | One Week Later | Before Water Resistance Test | | After Water Resistance Test | |
| Kind | (nm) | (g) | (g) | (g) | SPF | UVAPF | Emulsification | | SPF | UVAPF | SPF | UVAPF |
| Example 8 | 25 | 25 | 50 | — | 25 | 31 | 14 | ○ | ○ | 38 | 17 | 35 | 16 |
| Example 9 | 25 | 25 | 50 | — | 25 | 20 | 11 | ○ | ○ | 37 | 15 | 33 | 13 |
| Example 10 | 25 | 25 | 50 | — | 25 | 21 | 10 | ○ | ○ | 37 | 14 | 33 | 12 |

TABLE 7

| Emulsion Composition | | | | | | |
|---|---|---|---|---|---|---|
| Oil Phase | | | | | | |
| Inorganic Powder Composite | | | | | Oil Phase Dispersoid Evaluation Ultraviolet Ray Shielding | |
| | Average Primary Particle Size | Oil D5 oil | Emulsifying Agent KF-6028P | Water Phase Water | | |
| Kind | (nm) | (g) | (g) | (g) | SPF | UVAPF |
| Comparative Example 6 | 25 | 25 | 50 | — | 25 | 32 | 16 |
| Example 11 | 25 | 25 | 50 | — | 25 | 27 | 13 |
| Example 12 | 25 | 25 | 50 | — | 25 | 25 | 10 |
| Example 13 | 25 | 25 | 50 | — | 25 | 20 | 11 |
| Example 14 | 25 | 25 | 50 | — | 25 | 22 | 12 |
| Example 15 | 25 | 25 | 50 | — | 25 | 18 | 9 |
| Comparative | 25 | 25 | 50 | — | 25 | Unmeasurable | Unmeasurable |

TABLE 7-continued

| | | | W/O Emulsion Evaluation | | | | |
|---|---|---|---|---|---|---|---|
| | Emulsification Stability | | Water Resistance | | | | |
| | Immediately After | One Week Later | Before Water Resistance Test | | After Water Resistance Test | | |
| Kind | Emulsification | | SPF | UVAPF | SPF | UVAPF | |
| Example 7 | | | since no dispersion was made. | since no dispersion was made. | | | |
| Comparative Example 6 | x | x | Unmeasurable since no emulsification was made. | Unmeasurable since no emulsification was made. | Unmeasurable since no emulsification was made. | Unmeasurable since no emulsification was made. | |
| Example 11 | ○ | x | 34 | 16 | 30 | 14 | |
| Example 12 | ○ | ○ | 32 | 13 | 26 | 9 | |
| Example 13 | ○ | ○ | 40 | 14 | 38 | 12 | |
| Example 14 | ○ | x | 40 | 15 | 35 | 14 | |
| Example 15 | ○ | x | 28 | 12 | 22 | 8 | |
| Comparative Example 7 | x | x | Unmeasurable since no emulsification was made. | Unmeasurable since no emulsification was made. | Unmeasurable since no emulsification was made. | Unmeasurable since no emulsification was made. | |

TABLE 8

| | Emulsion Composition | | | | | | | | | | | | |
|---|---|---|---|---|---|---|---|---|---|---|---|---|---|
| | Oil Phase | | | | | | | W/O Emulsion Evaluation | | | | | |
| | Inorganic Powder Composite | | | | | | | | | | | | |
| | Average Primary Particle Size | Oil D5 oil | Emulsifying Agent KF-6028P | Water Phase Water | Oil Phase Dispersoid Evaluation Ultraviolet Ray Shielding | | Emulsification Stability | | Water Resistance | | | | |
| | | | | | | | Immediately After | One Week Later | Before Water Resistance Test | | After Water Resistance Test | | |
| Kind | (nm) | (g) | (g) | (g) | (g) | SPF | UVAPF | Emulsification | | SPF | UVAPF | SPF | UVAPF |
| Example 16 | 25 | 25 | 50 | — | 25 | 30 | 13 | ○ | ○ | 38 | 16 | 35 | 16 |
| Example 17 | 25 | 25 | 50 | — | 25 | 31 | 14 | ○ | ○ | 37 | 17 | 34 | 15 |
| Example 18 | 25 | 25 | 50 | — | 25 | 29 | 14 | ○ | ○ | 38 | 17 | 34 | 16 |
| Example 19 | 25 | 25 | 50 | — | 25 | 30 | 13 | ○ | ○ | 38 | 16 | 34 | 15 |
| Example 20 | 25 | 25 | 50 | — | 25 | 29 | 14 | ○ | ○ | 36 | 17 | 33 | 15 |

As shown in Tables 5 to 8, any of the emulsion compositions prepared by using the inorganic powder composites in Examples was emulsified at least immediately after emulsification work even without adding the emulsifying agent. In particular, in each of Examples 1 to 10, 12, 13, and 16 to 20, the emulsified state was maintained also immediately after the emulsification and also after the storage for one week.

(Water Resistance Test)

Next, water resistance of each of the emulsion compositions was checked.

First, 1.3 mg/cm$^2$ of the emulsion obtained as described above was applied to HELIOPLATE HD6 based on an SPF measurement method (ISO 24443). Drying was conducted for 30 minutes and thereafter, an SPF and a UVAPF were measured. The measured values are shown in Tables 5 to 8 as water resistance before a water resistance test.

Next, ion exchange water was poured into a beaker, and the HELIOPLATE with the emulsion applied was immersed therein for 80 minutes at 30° C. without agitating. Drying was conducted for 30 minutes and thereafter, the SPF and the UVAPF were measured. The measured values are shown in Tables 5 to 8 as water resistance after the water resistance test.

As shown in Tables 5 to 8, any of the inorganic powder composites in Examples 1 to 20 maintained favorable ultraviolet ray shielding properties even after the water resistance test.

(Comparison of Ultraviolet Ray Absorbance and SPF Before and After Emulsification)

Comparison of ultraviolet ray absorbance of the inorganic powder composites in Example 1 and Comparative Example 2 before and after the emulsification was made. Each of oil phase dispersions (specimens before the emulsification) was obtained by adding 25 g of the powder to 75 g of the decamethylcyclopentasiloxane and dispersing the resultant for three minutes at 3000 rpm by a disperser. In addition, the emulsion compositions prepared in the above-described emulsification stability test were used as specimens after the emulsification, and 1.3 mg/cm² of each of these specimens was applied to the HELIOPLATE HD6 based on the SPF measurement method (ISO 24443). Drying was conducted for 30 minutes and thereafter, the absorbance was measured. Results are shown in FIGS. 1 and 2.

Figure 2:
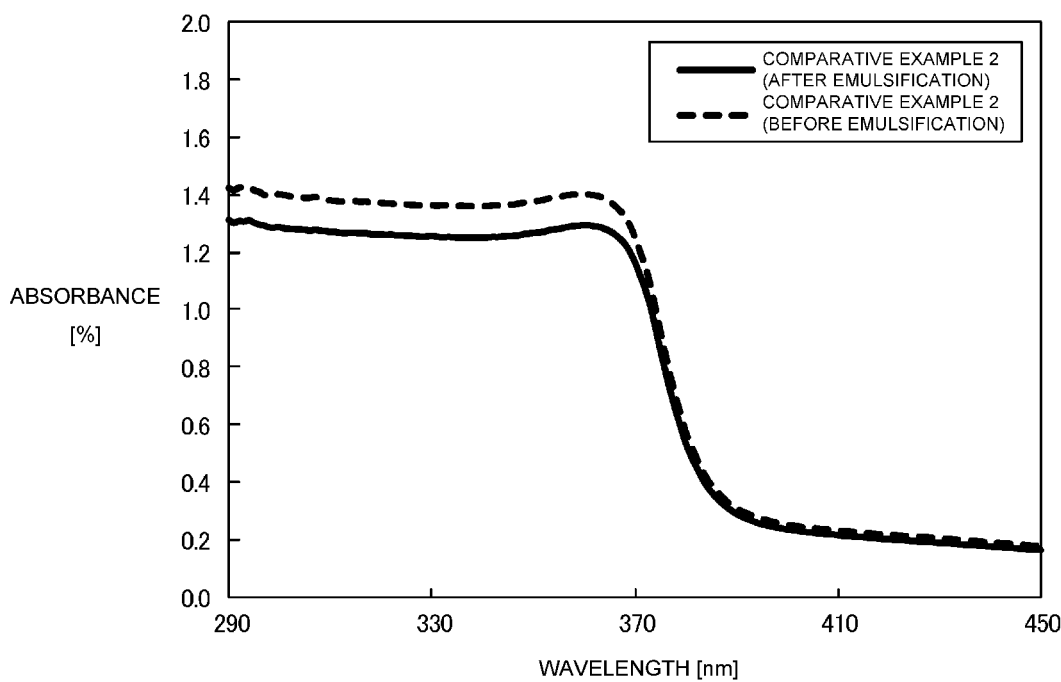
FIG. 2 is a graph showing absorbance of an oil phase at 290 nm to 450 nm before emulsification and absorbance of the oil phase at 290 nm to 450 nm after the emulsification in Comparative Example 2.

As shown in FIGS. 1 and 2, although values of the SPF of the inorganic powder composite in Example 1 and the inorganic powder composite in Comparative Example 2 before the emulsification (oil phase dispersions) were approximately the same as each other, the SPF in Comparative Example 2 after the emulsification was reduced and the SPF in Example 1 after the emulsification was greatly enhanced.

In addition, as to Examples and Comparative Examples, similarly, specimens before and after the emulsification were prepared, and the SPF and the UVAPF were measured. Ratios of the SPF of the emulsions to the SPF of the oil phase dispersions and ratios of the UVAPF of the emulsion to the UVAPF of the oil phase dispersions are shown in Table 9. Note that as to the specimens which were not emulsified, values of ratios of the SPF and values of ratios of the UVAPF are not shown therein.

TABLE 9

|  | SPF Ratio | UVAPF Ratio |
|---|---|---|
| Example 1 | 1.9 | 1.3 |
| Example 2 | 1.9 | 1.1 |
| Example 3 | 2.0 | 1.3 |
| Example 4 | 2.0 | 1.5 |
| Example 5 | 1.9 | 1.3 |
| Example 6 | 1.9 | 1.1 |
| Example 7 | 1.3 | 0.7 |
| Comparative Example 1 | 0.9 | 0.9 |
| Comparative Example 1A | — | — |
| Comparative Example 2 | 0.9 | 0.9 |
| Comparative Example 2A | — | — |
| Comparative Example 3 | — | — |
| Comparative Example 4 | — | — |
| Comparative Example 5 | — | — |
| Example 8 | 1.3 | 1.3 |
| Example 9 | 1.9 | 1.4 |
| Example 10 | 1.8 | 1.4 |
| Comparative Example 6 | — | — |
| Example 11 | 1.3 | 1.3 |
| Example 12 | 1.3 | 1.3 |
| Example 13 | 2.0 | 1.3 |
| Example 14 | 1.8 | 1.3 |
| Example 15 | 1.6 | 1.3 |
| Comparative Example 7 | — | — |
| Example 16 | 1.3 | 1.2 |
| Example 17 | 1.2 | 1.2 |
| Example 18 | 1.3 | 1.2 |
| Example 19 | 1.3 | 1.2 |
| Example 20 | 1.2 | 1.2 |

As is clear from Table 9, in any of Examples 1 to 20, any of the ratios of the SPF of the emulsions to the SPF of the oil phase dispersions was one or more, that is, the SPF of the emulsion was larger than the SPF of the oil phase dispersion. In particular, in each of Examples 1 to 6, 9, 10, and 13 to 15, the SPF of the emulsion was 1.5 or more times as large as the SPF of the oil phase dispersion. On the other hand, in any of Comparative Examples, the SPF of the emulsion was lower than the SPF of the oil phase dispersion.

From the above-described results, it is preferable that the inorganic powder composite according to the present invention includes: 90% to 98% by weight of the inorganic powder; 0.5% to 5.0% by weight of the first hydrophobic treatment agent, or more preferably, 1.0% to 4.0% by weight thereof; 0.5% to 5.0% by weight of the second hydrophobic treatment agent, or more preferably, 1.0% to 4.0% by weight thereof; and 0.5% to 6.0% by weight of the hydrophilic treatment agent in terms of $SiO_2$, or more preferably, 1.0% to 4.0% by weight thereof in terms thereof. In addition, it is preferable that the ratio between the total weight of the first hydrophobic treatment agent and the second hydrophobic treatment agent and the weight of the hydrophilic treatment agent, that is, the value of the total weight of the first hydrophobic treatment agent and the second hydrophobic treatment agent/the weight of the hydrophilic treatment agent is 0.2 to 6.0 and it is more preferable that the above-mentioned value is 0.8 to 2.5.

In addition, it is preferable that when the emulsion is obtained by adding 25 g of the inorganic powder composite to 50 g of the decamethylcyclopentasiloxane, dispersing the resultant for three minutes at 3000 rpm by means of the disperser to thereby obtain the oil phase dispersion, adding 25 g of the water to the oil phase dispersion, and emulsifying the resultant for two minutes at 3000 rpm by means of the disperser, the emulsion of the inorganic powder composite according to the present invention maintains the emulsified state after the emulsion has been stored at 50° C. for one week.

In addition, it is preferable that the SPF of the emulsion of the inorganic powder composite according to the present invention is 1.5 times or more as large as the SPF of the oil phase dispersion obtained by adding 25 g of the inorganic powder composite to 75 g of the decamethylcyclopentasiloxane and dispersing the resultant for three minutes at 3000 rpm by means of the disperser.

(Sunscreen Cosmetic)

By using the inorganic powder composite in Example 1, a water-in-oil type sunscreen cosmetic (sunscreen cosmetic 1) was prepared in a composition shown in Table 10.

TABLE 10

| Oil Phase | Inorganic Powder Composite in Example 1 | 20.0 wt % |
|---|---|---|
|  | hydrophobic treatment titanium oxide (Ingredients) | 2.0 wt % |
|  | titanium oxide | (1.3 wt %) |
|  | aluminum hydroxide | (0.2 wt %) |
|  | hydrous silica | (0.1 wt %) |
|  | triethoxycaprylylsilane | (0.4 wt %) |
|  | hydrophobic treatment zinc oxide (Ingredients) | 10.0 wt % |
|  | zinc oxide | (9.2 wt %) |
|  | triethoxycaprylylsilane | (0.8 wt %) |
|  | polymethylsilsesquioxane | 2.0 wt % |
|  | hydrogenated polyisobutene | 10.0 wt % |
|  | dimethicone | 5.9 wt % |
|  | ethylhexyl methoxycinnamate | 4.0 wt % |
|  | cyclopentasiloxane | 26.0 wt % |
|  | dibutylhydroxytoluene | 0.1 wt % |
| Water Phase | water | 15.9 wt % |
|  | sodium chloride | 1.0 wt % |

TABLE 10-continued

| | | |
|---|---|---|
| | methylparaben | 0.1 wt % |
| | butylene glycol | 3.0 wt % |
| | Total | 100.0 wt % |

By using the inorganic powder composite in Example 1, a water-in-oil type sunscreen cosmetic (sunscreen cosmetic 2) was prepared in a composition shown in Table 11.

TABLE 11

| | | |
|---|---|---|
| Oil phase | Inorganic Powder Composite in Example 1 | 25.0 wt % |
| | polymethylsilsesquioxane | 2.0 wt % |
| | hydrogenated polyisobutene | 10.0 wt % |
| | dimethicone | 5.9 wt % |
| | cyclopentasiloxane | 32.0 wt % |
| | dibutylhydroxytoluene | 0.1 wt % |
| Water Phase | water | 15.9 wt % |
| | sodium chloride | 1.0 wt % |
| | methylparaben | 0.1 wt % |
| | butylene glycol | 3.0 wt % |
| | hydrophiliatitanium oxide | 5.0 wt % |
| | Total | 100.0 wt % |

(Emulsification Function)

An emulsified state of each of the sunscreen cosmetics 1 and 2 was visually checked. Determination criteria were as follows. Results are shown in Table 12.

○: A water-in-oil type emulsified state is formed.

x: Emulsification is impossible and separation between an oil phase and a water phase is visually checked.

As to each of the sunscreen cosmetics 1 and 2, an emulsified state was visually checked immediately after the preparation and after still standing at 50° C. for one month. Determination criteria are as follows. Results are shown in Table 12.

(Storage Stability)

○: A water-in-oil type emulsified state is maintained.

x: Separation between an oil phase and a water phase is visually checked.

TABLE 12

| | Sunscreen Cosmetic | |
|---|---|---|
| | 1 | 2 |
| Emulsification Function | ○ | ○ |
| Storage Stability | ○ | ○ |

As shown in Table 12, by using the inorganic powder composite of the present invention, stable emulsification can be made without using the emulsifying agent and a water-in-oil type sunscreen cosmetic having high storage stability can be provided.

The above-described embodiment and Examples are to be considered in all respects only as illustrative and not restrictive. It is intended that the scope of the present invention is, therefore, indicated by the appended claims rather than the foregoing description of the embodiment and Examples and that all modifications and variations coming within the meaning and equivalency range of the appended claims are embraced within their scope.

The invention claimed is:

1. An inorganic powder composite including:
    an inorganic powder; a first hydrophobic treatment agent, a second hydrophobic treatment agent, and a hydrophilic treatment agent, which cover at least one part of a surface of the inorganic powder, wherein the first hydrophobic treatment agent is a silicon compound, the second hydrophobic treatment agent is a fatty acid, and the hydrophilic treatment agent is hydrous silica, wherein the inorganic powder composite has the property to be able to form an emulsion without the presence of an emulsifying agent.

2. The inorganic powder composite according to claim 1, wherein the inorganic powder has ultraviolet ray shielding effects.

3. The inorganic powder composite according to claim 1, wherein the inorganic powder is zinc oxide.

4. The inorganic powder composite according to claim 1, wherein the first hydrophobic treatment agent is hydrogen dimethicone or triethoxycaprylylsilane.

5. The inorganic powder composite according to claim 1, wherein the second hydrophobic treatment agent is isostearic acid.

6. The inorganic powder composite according to claim 1, wherein the first hydrophobic treatment agent is hydrogen dimethicone or triethoxycaprylylsilane and the second hydrophobic treatment agent is isostearic acid.

7. The inorganic powder composite according to claim 1, wherein an average primary particle size of the inorganic powder is less than 80 nm.

8. The inorganic powder composite according to claim 1, including
    90% to 98% by weight based on the total weight of the composition of the inorganic powder,
    0.5% to 5.0% by weight based on the total weight of the composition of the first hydrophobic treatment agent,
    0.5% to 5.0% by weight based on the total weight of the composition of the second hydrophobic treatment agent, and
    0.5% to 6.0% by weight based on the total weight of the composition of the hydrophilic treatment agent in terms of $SiO_2$.

9. An inorganic powder composite including:
    an inorganic powder; a first hydrophobic treatment agent, a second hydrophobic treatment agent, and a hydrophilic treatment ag which cover at least one part of a surface of the inorganic powder, wherein the first hydrophobic treatment agent is a silicon compound, the second hydrophobic treatment agent is a fatty acid, and the hydrophilic treatment agent is hydrous silica, wherein the inorganic powder composite has the property to be able to form an emulsion without the presence of an emulsifying agent, wherein when an oil phase dispersion is obtained by adding 25 g of the inorganic powder composite to 50 g of decamethylcyclopentasiloxane, dispersing a resultant for three minutes at 3000 rpm by a disperser and an emulsion is obtained by adding 25 g of water to the oil phase dispersion and emulsifying a resultant for two minutes at 3000 rpm by the disperser, the emulsion maintains an emulsified state after the emulsion has been stored at 50° C. for one week.

10. The inorganic powder composite according to claim 9, wherein an SPF of the emulsion is 1.5 times or more as large as an SPF of an oil phase dispersion being obtained by adding 25 g of the inorganic powder composite to 75 g of the decamethylcyclopentasiloxane and dispersing a resultant for three minutes at 3000 rpm by the disperser.

11. A water-in-oil type emulsion composition including the inorganic powder composite according to claim 1.

12. A water-in-oil type emulsion composition including the inorganic powder composite according to claim 1 and containing no surfactant.

13. The water-in-oil type emulsion composition according to claim 11, further comprising at least one of surface-treated titanium oxide, surface-treated zinc oxide, and an ultraviolet ray absorbing agent.

14. The water-in-oil type emulsion composition according to claim 13, wherein a surface treatment agent of the surface-treated titanium oxide or the surface-treated zinc oxide is at least one of hydrous silica, aluminum hydroxide, alginic acid, a fatty acid, silicone oil, and a silane coupling agent.

15. The water-in-oil type emulsion composition according to claim 14, wherein the fatty acid is at least one of lauric acid, myristic acid, palmitic acid, isostearic acid, and stearic acid.

16. The water-in-oil type emulsion composition according to claim 14, wherein the silicone oil is at least one of methicone, dimethicone, and hydrogen dimethicone.

17. The water-in-oil type emulsion composition according to claim 14, wherein the silane coupling agent is triethoxycaprylylsilane.

18. The water-in-oil type emulsion composition according to claim 13, wherein the ultraviolet ray absorbing agent is at least one of a triazine system, a benzotriazole system, a benzophenone system, a merocyanine system, a cyanine system, a dibenzoyl-methane system, a cinnamic acid system, a cyanoacrylate system, and a benzoic acid ester system.

19. The water-in-oil type emulsion composition according to claim 11, wherein the water-in-oil type emulsion composition is a sunscreen cosmetic.

20. A method for manufacturing an inorganic powder composite according to claim 1, the method comprising
a step of subjecting an inorganic powder to surface treatment by a first hydrophobic treatment agent, a second hydrophobic treatment agent, and a hydrophilic treatment agent, wherein
the first hydrophobic treatment agent is a silicon compound,
the second hydrophobic treatment agent is a fatty acid, and
the hydrophilic treatment agent is hydrous silica.

21. The method for manufacturing an inorganic powder composite according to claim 20, wherein the first hydrophobic treatment agent is hydrogen dimethicone or triethoxycaprylylsilane and the second hydrophobic treatment agent is isostearic acid.

22. The water-in-oil type emulsion composition according to claim 11, which does not include an emulsifier, and includes the inorganic powder composite according to claim 1.

* * * * *